(12) United States Patent
Johnson et al.

(10) Patent No.: US 6,528,792 B2
(45) Date of Patent: *Mar. 4, 2003

(54) GAS DETECTION APPARATUS USING A COMBINED INFRARED SOURCE AND HIGH TEMPERATURE BOLOMETER

(75) Inventors: Edward A. Johnson, Bedford, MA (US); William Andrew Bodkin, Needham, MA (US)

(73) Assignee: Ion Optics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/123,274

(22) Filed: Apr. 16, 2002

(65) Prior Publication Data

US 2002/0109095 A1 Aug. 15, 2002

Related U.S. Application Data

(63) Continuation of application No. 09/555,861, filed as application No. PCT/US98/25771 on Dec. 4, 1998, now Pat. No. 6,373,056.
(60) Provisional application No. 60/067,713, filed on Dec. 4, 1997, and provisional application No. 60/094,602, filed on Jul. 30, 1998.

(51) Int. Cl.$^7$ ................ G01J 5/02; G01J 5/00
(52) U.S. Cl. ................ 250/339.13; 250/338.3
(58) Field of Search .............. 250/338.3, 339.06, 250/339.13

(56) References Cited

U.S. PATENT DOCUMENTS 5,508,546 A * 4/1996 Zalameda et al. ........ 250/338.3
5,747,808 A * 5/1998 Wong .................... 250/339.13

* cited by examiner

*Primary Examiner*—Georgia Epps
*Assistant Examiner*—Alicia Harrington
(74) *Attorney, Agent, or Firm*—McDermott, Will & Emery

(57) ABSTRACT

An apparatus for detecting a gas having distinct infrared radiation absorption characteristics. The apparatus includes a spectral source/bolometer for conducting an electrical current and for producing an infrared radiation. The source/bolometer is disposed along an axis and has a temperature and a characteristic resistance, and the characteristic resistance is a predetermined function of the temperature. A return reflector is disposed along the axis beyond the gas such that at least a portion of the infrared radiation passing through the gas is reflected back through the gas to the source/bolometer. The apparatus also includes a driver/detector for driving a current through the source/bolometer, for determining the characteristic resistance, and for detecting the gas from a variation of the characteristic resistance.

15 Claims, 4 Drawing Sheets

US 6,528,792 B2

GAS DETECTION APPARATUS USING A COMBINED INFRARED SOURCE AND HIGH TEMPERATURE BOLOMETER

CROSS-REFERENCE TO RELATED APPLICATIONS

The present application is a continuation of U.S. patent application Ser. No. 09/555,861, filed on Feb. 2, 2001, now U.S. Pat. No. 6,373,056, which claims priority to International Patent Application No. PCT/US98/25771, which is based on provisional application, U.S. Ser. No. 60/067,713, filed on Dec. 4, 1997 by William Andrew Bodkin, entitled INFRARED SPECTRAGRAPHIC SYSTEM, and U.S. Provisional Patent Application Serial No. 60/094,602, filed on Jul. 30, 1998, by Edward A. Johnson.

This application is related to U.S. Provisional Patent Application Serial No. 60/096,133 which is hereby incorporated by reference.

STATEMENT REGARDING FEDERALLY SPONSORED RESEARCH

Not Applicable

REFERENCE TO MICROFICHE APPENDIX

Not Applicable

FIELD OF THE INVENTION

The field of the invention is electro-optical radiation sources and detectors, and more particularly, to an apparatus that simultaneously functions as an electro-optical radiation source and an electro-optical radiation detector.

BACKGROUND OF THE INVENTION

Non-dispersive Infrared (NDIR) techniques utilizing the characteristic absorption bands of gases in the infrared have long been considered as one of the best methods for composite gas measurement. These techniques take advantage of the fact that various gases exhibit substantial absorption at specific wavelengths in the infrared radiation spectrum. The term "non-dispersive" refers to the type of apparatus incorporating this particular measurement technique, typically including a narrow band pass interference filter (as opposed to a "dispersive" element, such as a prism or a diffraction grating) to isolate and pass radiation in a particular wavelength band from a spectrally broad band infrared source. The gas concentration is discerned from the detected intensity modulation of source radiation that is passed by the filter coincident in wavelength with a strong absorption band of the gas to be measured.

A prior art NDIR gas analyzer typically includes a discrete infrared source with a motor-driven mechanical chopper to modulate the source so that synchronous detection may be used to discriminate spurious infrared radiation from surroundings; a pump to push gas through a sample chamber; a narrow band-pass interference filter; a sensitive infrared detector, and infrared optics/windows to focus the infrared energy from the source onto the detector. Although the NDIR gas measurement technique is recognized as one of the most effective methodologies for composite gas measurement available, it has not enjoyed wide application because of its complexity and high cost of implementation.

Infrared absorption instruments traditionally contain a source of infrared radiation, a means of spectral selection for the gas under study, an absorption cell with associated gas sample handling and/or conditioning, any necessary optics, a sensitive infrared detector, and associated signal processing electronics. A typical source of infrared radiation includes an incandescent filament or a thin film conductor. The emissions spectrum of the infrared source may be tailored via surface texturing techniques, as are described in U.S. Pat. No. 5,838,016. The invention simplifies and reduces the cost of an infrared instrument by integrating the function of the infrared source and infrared detector into a single self-supporting thin-film bolometer element. This element is packaged with inexpensive molded plastic optics and a conventional spectral filter to make a transistor-size "sensor engine." Combined with a simple reflector plate to define the gas sampling region, this sensor engine provides a complete gas sensor instrument which is extremely inexpensive and which will approach the sensitivity of conventional infrared absorption instruments.

SUMMARY OF THE INVENTION

The present invention is an apparatus for detecting a gas having a distinct infrared radiation absorption characteristics. The apparatus includes a spectral source/bolometer for conducting an electrical current and for producing an infrared radiation. The source/bolometer is disposed along an axis and has a temperature and a characteristic resistance; the characteristic resistance is a predetermined function of the temperature. The apparatus further includes a concentrating reflector for directing the infrared radiation along the axis, first through a spectral filter and then through the gas. The apparatus also includes a return reflector disposed along the axis beyond the spectral filter and the gas, such that at least a portion of the infrared radiation passing through the filter and the gas is reflected back through the gas and the filter to the source/bolometer. The apparatus further includes a driver/detector for driving a current through the source/bolometer, for determining the characteristic resistance, and for detecting the gas from a variation of the characteristic resistance.

In one embodiment, the source/bolometer includes a thin-film conductor.

In another embodiment, the source/bolometer includes a filament conductor.

In another embodiment, the source/bolometer includes surface texturing so as to tailor a spectral characteristic of the infrared radiation.

In a further embodiment, the concentrating reflector is disposed about the axis so as to form a first aperture along the axis and a second aperture along the axis, the source/bolometer is disposed at the first aperture and the spectral filter is disposed at the second aperture.

In another embodiment, the concentrating reflector forms a compound parabolic concentrator.

In another embodiment, the return reflector defines a gas sampling region.

In another embodiment, the return reflector includes a flat reflective surface disposed substantially perpendicular to the axis.

In another embodiment, the return reflector includes a contoured reflective surface disposed substantially about the axis.

In one embodiment, the contoured reflective surface includes a parabolic surface.

In another embodiment, the spectral filter substantially passes infrared radiation within a first passband and substantially blocks infrared radiation outside of the first passband.

In a further embodiment, the spectral filter includes a micromesh reflective filter.

In another embodiment, the micromesh reflective filter is fabricated using micro-electro-mechanical systems technology.

In yet another embodiment, the driver/detector includes a Wheatstone bridge circuit having a first resistor pair and a second resistor pair, wherein a first resistor of the first resistor pair includes the source/bolometer.

In another embodiment, a second resistor of the first resistor pair includes a blind source/bolometer being identical to the source/bolometer and filtered at a second passband.

In another embodiment, a ratio of the first resistor pair is substantially equal to a ratio of the second resistor pair.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENT

Figure 1:
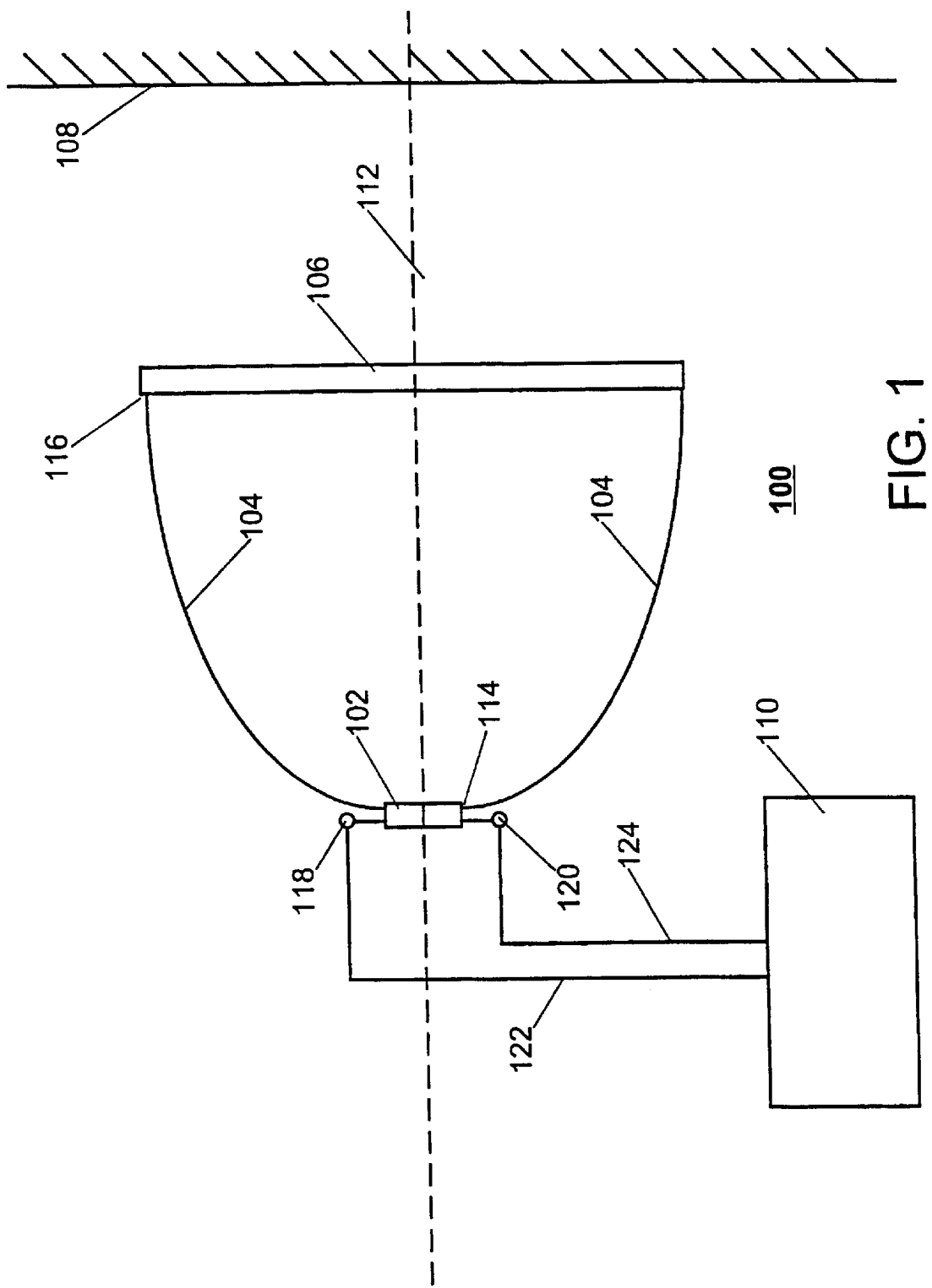
FIG. 1 illustrates one preferred embodiment of a combined infrared source and sensor.

Referring now to the drawings, FIG. 1 illustrates one preferred embodiment of a combined infrared source and sensor 100 including a spectral source/bolometer 102, a concentrating reflector 104, a spectral filter 106, a return reflector 108 and a driver/detector circuit 110. The concentrating reflector 104 is disposed substantially symmetrically about an axis 112 so as to form a first aperture 114 and a second aperture 116. The source/bolometer 102 is disposed along the axis 112 at the first aperture 114 so as to direct the infrared radiation from the source/bolometer 102 along an axis 112 toward the second aperture 116. The return reflector 108 is disposed along the axis 112 such that the infrared radiation from the source/bolometer 102 directed along the axis 112 is reflected back along the axis 112 through the second aperture 116 toward the source/bolometer 102. The spectral filter 106 is disposed along the axis 112 at the second aperture 116. Infrared radiation passing through the second aperture 116 (either from the source/bolometer 102 to the return reflector 108, or vice versa) passes through and may be modified by the spectral filter 106. The driver/detector circuit 110 is electrically coupled to a first terminal 118 and a second terminal 120 of the source/bolometer 102 via a first electrical conductor 122 and a second electrical conductor 124, respectively.

The spectral source/bolometer 102 may include a filament, a thin-film element or other infrared radiating components known to those in the art. The first terminal 118 and the second terminal 120 are electrically coupled to the source/bolometer 102 such that an external driver (e.g., the driver/detector circuit 110) can apply a voltage across the source/bolometer 102 via the first terminal 120 and the second terminal 122, thereby inducing current flow through the source/bolometer. In one preferred embodiment, the surface of the source/bolometer may be textured so as to selectively tailor the infrared emissions spectrum to substantially match the absorption characteristics of the target gas to be detected.

In the illustrated embodiment of the invention, the concentrating reflector 104 includes a parabolic reflector, although other reflector shapes (e.g., spherical, conical and custom contoured) may be used to adequately direct the infrared radiation from the source/bolometer 102 along the axis 112. Similarly, although the embodiment illustrated in FIG. 1 includes a flat reflector, other reflector shapes may be use. The spectral filter 106 may include any one of several conventional designs known to those in the art to achieve tight spectral control of the infrared emission. In general, the spectral filter 106 passes only infrared radiation that is within a predetermined passband. The predetermined passband is chosen as a function of the target gas to be detected.

The electrical resistance R of the source/bolometer 102 varies as a function of its equilibrium temperature T, i.e., $R = f\{T\}$. The function $f\{T\}$ may be determined empirically or analytically for a particular source/bolometer 102. For a given amount of input power applied to the source/bolometer 102, the equilibrium temperature T of the source/bolometer 102 is dependent upon how fast it cools, and the cooling rate of the source/bolometer 102 is dependent on the optical absorption characteristics of its immediate environment. In general, different gases are known to each exhibit distinct optical absorption characteristics. The spectral filter 106 may be selected such that the infrared source and sensor 100 forms a tuned cavity band emitter corresponding to the absorption characteristics of the gas under study. Thus, the gas may be detected in the presence of the source/bolometer 102 by monitoring the resistance R of the source/bolometer 102.

Figure 2:
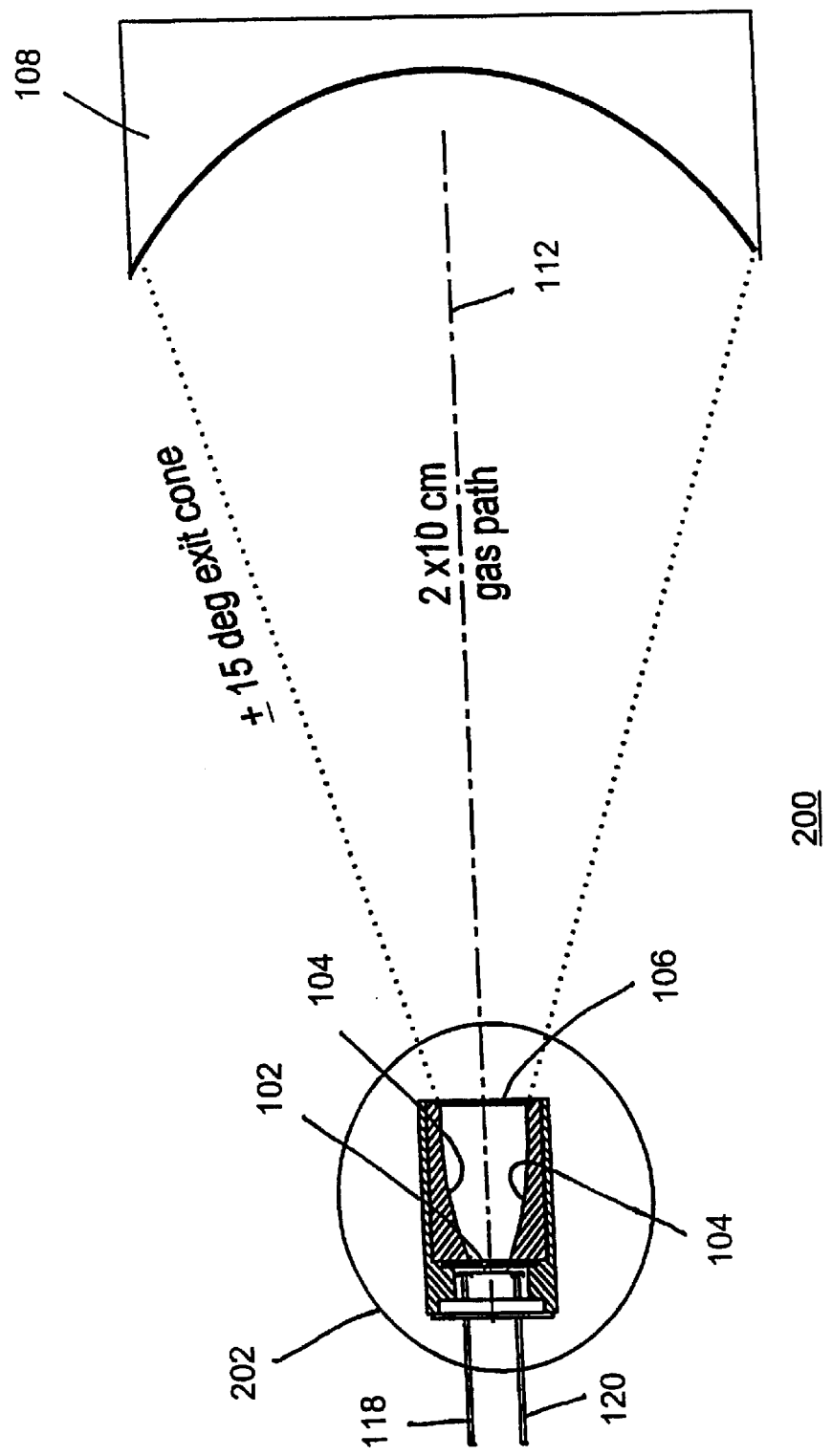
FIG. 2 illustrates another embodiment of the combined infrared source and sensor shown in FIG. 1.

FIG. 2 illustrates another embodiment of the present invention, that forms an infrared gas monitoring component 200 of an integrated on-board exhaust NOx meter (where x is a positive non-zero integer). This embodiment utilizes silicon micro-machining technology to construct a sensor that is radically simpler than conventional infrared absorption instruments. This embodiment simplifies and reduces the cost of an infrared absorption instrument by integrating the function of the infrared source and infrared detector into a single self-supporting thin-film source/bolometer 102. The source/bolometer 102 includes inexpensive molded plastic optics and a conventional spectral filter 106 to make a transistor-size sensor engine 202. Combined with a simple reflector plate to define the gas sampling region, this sensor engine provides a complete gas sensor instrument which is extremely inexpensive and which will approach the sensitivity of conventional infrared absorption instruments.

The embodiment of FIG. 2 illustrates a novel, low-cost infrared gas sensor using a thin-film source/bolometer 102 in an open path atmospheric gas measurement. As described herein, the source/bolometer 102 reaches radiative equilibrium with its surroundings at a slightly lower temperature if gas absorption frustrates light re-imaging source/bolometer 102. The concentrating reflector 104, in this case a compound parabolic concentrator, defines a relatively narrow illumination cone (+/−15 degrees about the axis 118) and the passive return reflector 108 is contoured to provide a pupil-image of the spectral filter 106 onto itself. The entire sensor engine 202 can be mounted in a substantially small package, e.g., on a TO-8 transistor header.

Tight spectral control of the infrared emission is important in making the source/bolometer 102 work well. The device is particularly effective if the amount of radiation absorbed by gas molecules under study is measurably large in terms of the overall thermal budget of the bolometer surface. Thus, a tuned cavity band emitter is preferably constructed with spectral resolution (dl/l) around 0.1, roughly the performance achieved to date with micromesh reflective filters. This increases the conversion efficiency to nearly 15% for the NOx application. This level of surface topology (and therefore spectral) control, is achieved through micro-electro-mechanical systems (MEMS) technologies. An individual emitter die is packaged, together with individual infrared detector pixel elements and thin film interference filter windows in TO-8 transistor cans using standard process equipment.

Figure 3:
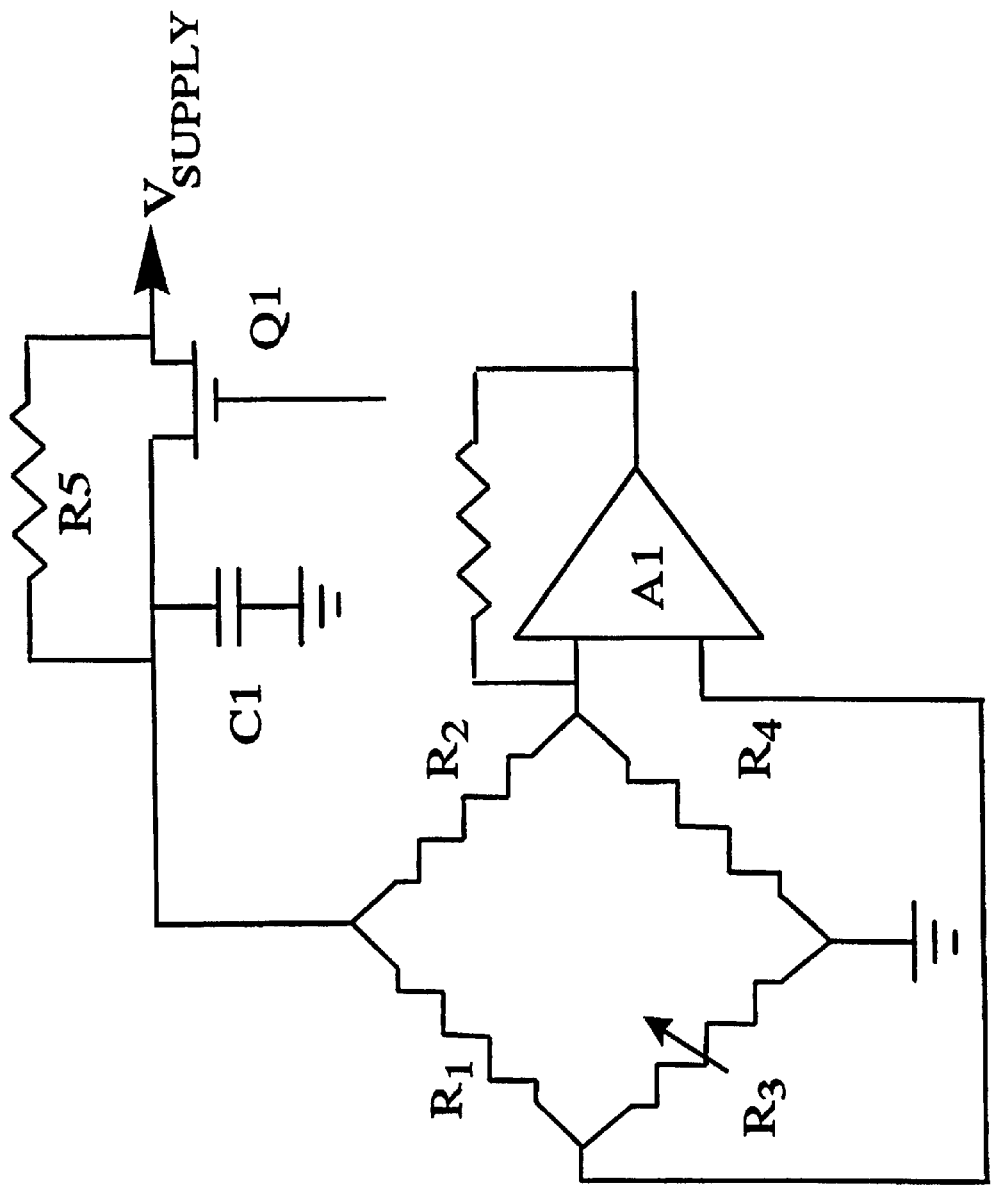
FIG. 3 illustrates a Wheatstone bridge used to drive the source/bolometer component of the source and sensor shown in FIG. 1; and, FIG. 4 shows a test configuration that incorporates the Wheatstone bridge of FIG. 3.
Figure 4:
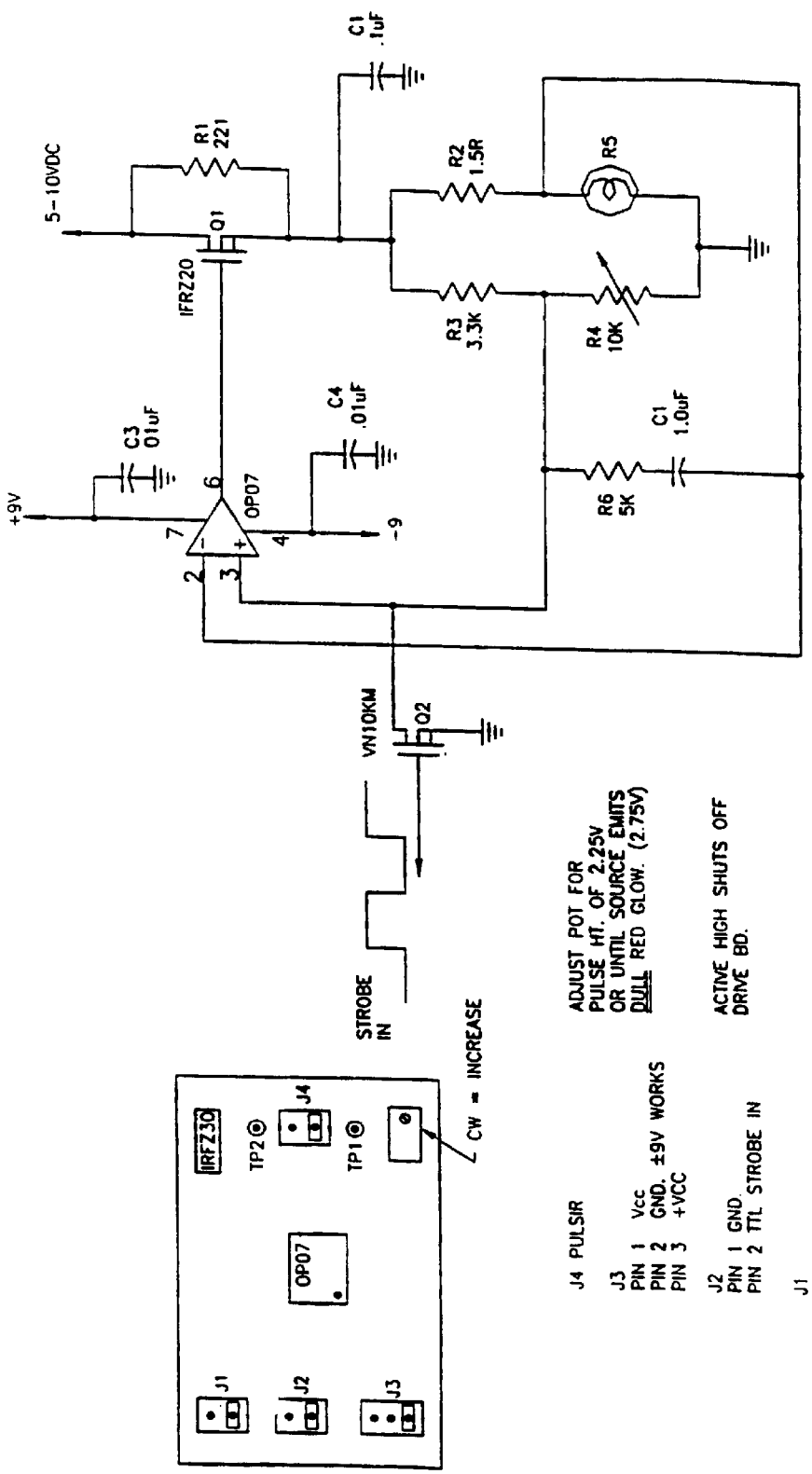

The embodiment illustrated in FIG. 2 uses drive and readout schemes having a microprocessor controlled, temperature-stabilized driver to determine resistance from drive current and drive voltage readings. The current and voltage information shows that incidental resistances (temperature coefficients in leads and packages and shunt resistors, for instance) do not overwhelm the small resistance changes used as a measurement parameter. The Wheatstone bridge 300 shown in FIG. 3, a straightforward analog control circuit, is used to drive the source/bolometer 102 and determine the incremental resistance values. The Wheatstone bridge is simple and accurate, is substantially insensitive to power supply variations and is relatively insensitive to temperature. The circuit is "resistor" programmable, but depends for stability on matching the ratio of resistors. In one form of the invention, an adjacent "blind" pixel, i.e., an identical bolometer element (a blind source/bolometer), filtered at some different waveband, is used as the resistor in the other leg of the bridge, allowing compensation for instrument and component temperatures and providing only a difference signal related to infrared absorption in the gas. The Wheatstone bridge provides a simple computer interface, and since it is implemented with relatively robust analog parts, it is not susceptible to radiation damage at high altitudes or in space. For the Wheatstone bridge 300 shown in FIG. 3, bridge is balanced when the ratio of the resistor pair R1 and R2 is substantially equal to the ratio of the resistor pair R3 and R4 (i.e., R1/R2=R3/R4), and to first order, temperate coefficients of R1 and R2 can be neglected if resistors are matched. The temperature coefficient of R3 is important but should have negligible effect across the relatively small change in temperature of the bolometer caused by the gas absorption. Preferably, the resistors are chosen so that the bridge is substantially balanced at the target operating temperature. The estimated errors from an analog readout of this circuit come from the amplifier input offset and input bias currents which introduce offset voltage or error term. FIG. 4 shows a test configuration that incorporates the Wheatstone bridge 300. Note that the component reference designations FIG. 4 do not correspond to those in FIG. 3.

An optics test bed has been used to evaluate different configurations and perform measurements of this embodiment. In an elevated ambient temperature environment (e.g., automotive), the device is operated as instrumented tube furnaces and to calibrate the infrared readings against a conventional gas analyzer.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. An apparatus for detecting a gas having distinct infrared radiation absorption characteristics, comprising:

a spectral source/bolometer for conducting an electrical current and for producing an infrared radiation, said source/bolometer being disposed along an axis and having a temperature and a characteristic resistance, said characteristic resistance being a predetermined function of said temperature;

a return reflector disposed along said axis beyond said gas, such that at least a portion of said infrared radiation passing through said gas is reflected back through said gas to said source/bolometer; and, a driver/detector for driving a current through said source/bolometer, for determining said characteristic resistance, and for detecting said gas from a variation of said characteristic resistance.

2. An apparatus according to claim 1, wherein said source/bolometer includes a thin-film conductor.

3. An apparatus according to claim 1, wherein said source/bolometer includes a filament conductor.

4. An apparatus according to claim 1, wherein said source/bolometer includes surface texturing tailored so as to have an emission spectrum substantially matched to said absorption characteristics.

5. An apparatus according to claim 1, further including a spectral filter disposed along said axis between said source/bolometer and said gas so as to tailor a spectral characteristic of said infrared radiation to substantially match said absorption characteristics.

6. An apparatus according to claim 1, wherein said return reflector defines a gas sampling region.

7. An apparatus according to claim 1, wherein said return reflector includes a flat reflective surface disposed substantially perpendicular to said axis.

8. An apparatus according to claim 1, wherein said return reflector includes a contoured reflective surface disposed substantially about said axis.

9. An apparatus according to claim 8, wherein said contoured reflective surface includes a parabolic surface.

10. An apparatus according to claim 5, wherein said spectral filter substantially passes infrared radiation within a first passband and substantially blocks infrared radiation outside of said first passband.

11. An apparatus according to claim 5, wherein said spectral filter includes a micromesh reflective filter.

12. An apparatus according to claim 11, wherein said micromesh reflective filter is fabricated using micro-electro-mechanical systems technology.

13. An apparatus according to claim 1, said driver/detector including a Wheatstone bridge circuit having a fist resistor pair and a second resistor pair, wherein a first resistor of said first resistor pair includes said source/bolometer.

14. An apparatus according to claim 13, wherein a second resistor of said first resistor pair includes a blind source/bolometer being identical to said source/bolometer and filtered at a second passband.

15. An apparatus according to claim 13, wherein a ratio of said first resistor pair is substantially equal to a ratio of said second resistor pair.

* * * * *